(12) United States Patent
Brooks et al.

(10) Patent No.: US 9,756,699 B2
(45) Date of Patent: Sep. 5, 2017

(54) LOW-POWER DATA ACQUISITION SYSTEM AND SENSOR INTERFACE

(71) Applicant: BROADCOM CORPORATION, Irvine, CA (US)

(72) Inventors: Todd Lee Brooks, Laguna Beach, CA (US); Xicheng Jiang, Irvine, CA (US); Iuri Mehr, Irvine, CA (US); David Joseph Stoops, Lake Forest, CA (US); Vinod Jayakumar, Irvine, CA (US); Min Gyu Kim, Irvine, CA (US); Hui Zheng, Irvine, CA (US); I-Ning Ku, Irvine, CA (US); Vinay Chandrasekhar, Irvine, CA (US); Yee Ling Cheung, Irvine, CA (US)

(73) Assignee: Avago Technologies General IP (Singapore) Pte. Ltd, Singapore (SG)

( * ) Notice: Subject to any disclaimer, the term of this patent is extended or adjusted under 35 U.S.C. 154(b) by 496 days.

(21) Appl. No.: 14/473,635

(22) Filed: Aug. 29, 2014

(65) Prior Publication Data
US 2015/0066438 A1    Mar. 5, 2015

Related U.S. Application Data

(60) Provisional application No. 61/872,075, filed on Aug. 30, 2013, provisional application No. 61/872,352, filed on Aug. 30, 2013.

(51) Int. Cl.
*H04B 15/00* (2006.01)
*H05B 33/08* (2006.01)
(Continued)

(52) U.S. Cl.
CPC ............. *H05B 33/089* (2013.01); *G01K 1/02* (2013.01); *G01R 19/0092* (2013.01);
(Continued)

(58) Field of Classification Search
CPC ......... G01J 1/44; G01K 1/02; G01R 19/0092; H03B 2202/022; H03B 5/20; H03K 4/502
See application file for complete search history.

(56) References Cited

U.S. PATENT DOCUMENTS

| 4,137,467 A | * | 1/1979 | Plog | G08B 23/00 327/66 |
| 5,498,986 A | * | 3/1996 | Manlove | H03K 5/249 327/337 |
| 5,977,803 A | * | 11/1999 | Tsugai | G01R 27/2605 327/337 |

OTHER PUBLICATIONS

Yang et al., 'Configurable Hardware-Efficient Interface Circuit for Multi-Sensor Microsystems', Oct. 2006, IEEE Publication, pp. 41-44.*

* cited by examiner

*Primary Examiner* — Elias Desta
(74) *Attorney, Agent, or Firm* — Garlick & Markison; Shayne X. Short

(57) ABSTRACT

A sensor interface includes on-chip relaxation oscillator circuit and a PLL that operate cooperatively to generate a highly accurate clock signal on-chip using low-power components. A photodiode generates a current signal based on an optical signal that is representative of a sensor signal. An ADC that operates based on the highly accurate clock signal generates a digital signal based on the current signal generated by the photodiode, and a processor processed the digital signal to estimate sensor data within the sensor signal. Examples of characteristics that may be sensed can include environmental characteristics (e.g., temperature, humidity, barometric pressure, etc.) and/or biomedical characteristics (e.g., body temperature, heart rate, respiratory rate, blood pressure, etc.). If desired, an amplifier processes the photodiode-provided current signal before it is provided (Continued)

to the ADC. Also, one or more CDACs that generate feedback currents may be used to reduce noise sensitivity of the sensor interface.

20 Claims, 8 Drawing Sheets

(51) Int. Cl.
*G01R 19/00* (2006.01)
*H03K 3/0231* (2006.01)
*G01K 1/02* (2006.01)
*A61B 5/01* (2006.01)
*A61B 5/024* (2006.01)
*A61B 5/08* (2006.01)
*A61B 5/021* (2006.01)
*G01J 1/44* (2006.01)

(52) U.S. Cl.
CPC .............. *H03K 3/0231* (2013.01); *A61B 5/01* (2013.01); *A61B 5/021* (2013.01); *A61B 5/024* (2013.01); *A61B 5/0816* (2013.01); *A61B 2562/06* (2013.01); *G01J 1/44* (2013.01)

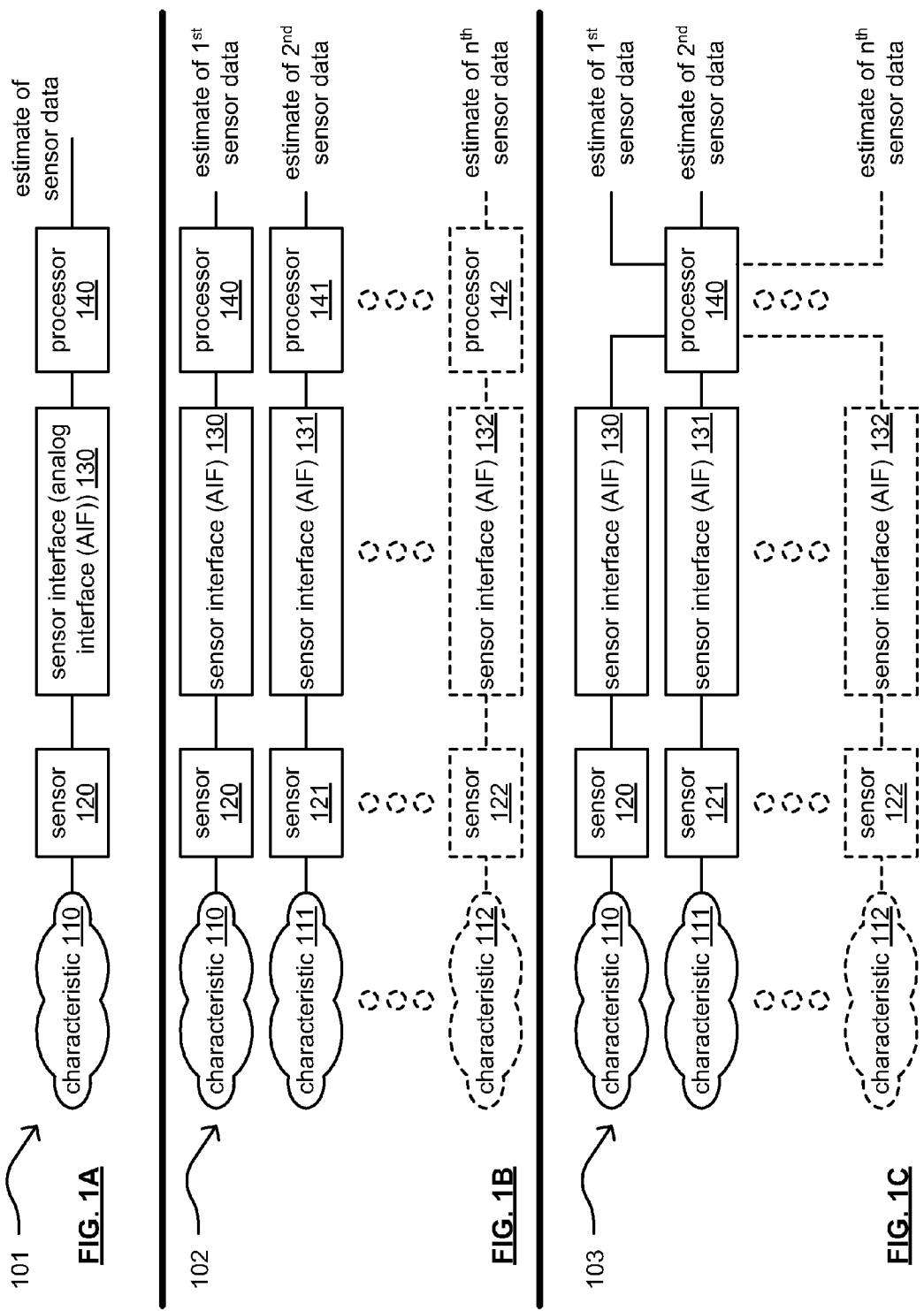

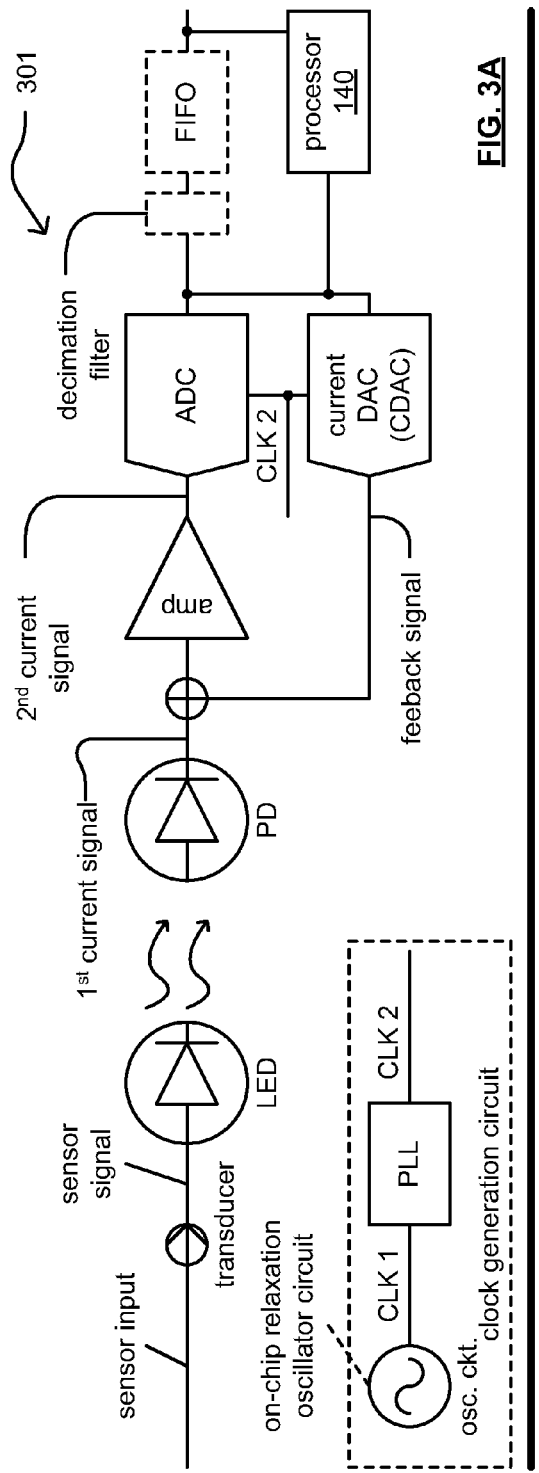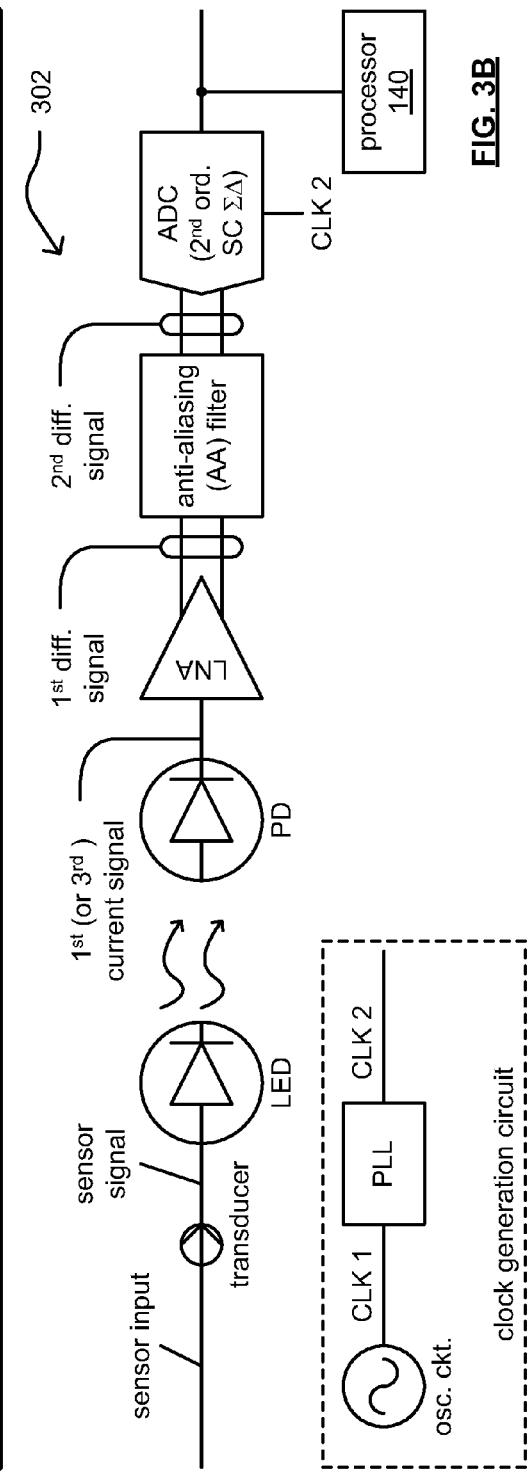
FIG. 3A
FIG. 3B

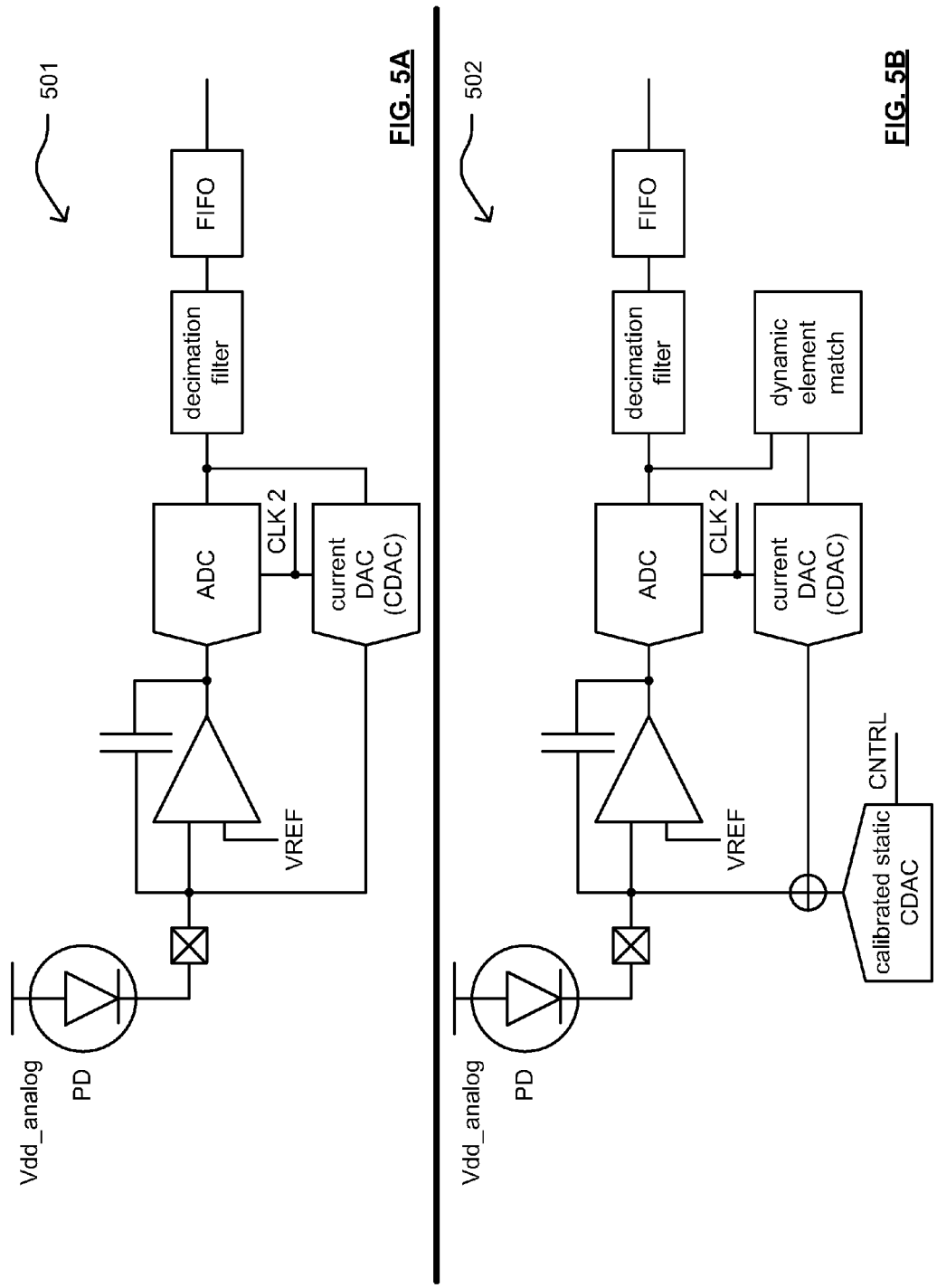

LOW-POWER DATA ACQUISITION SYSTEM AND SENSOR INTERFACE

CROSS REFERENCE TO RELATED PATENTS/PATENT APPLICATIONS

Provisional Priority Claims

The present U.S. Utility patent application claims priority pursuant to 35 U.S.C. §119(e) to U.S. Provisional Application No. 61/872,075, entitled "Low-power data acquisition system and sensor interface," filed Sep. 30, 2013; and U.S. Provisional Application No. 61/872,352, entitled "Low-power data acquisition system and sensor interface," filed Sep. 30, 2013, both of which are hereby incorporated herein by reference in their entirety and made part of the present U.S. Utility patent application for all purposes.

BACKGROUND

Technical Field

The present disclosure relates generally to communication systems; and, more particularly, to sensors and sensing functionality within such communication systems.

Description of Related Art

Sensor-based systems are implemented in a variety of applications. Examples of such systems include those that include one or more devices to monitor one or more characteristics within the system. However, there are many deficiencies within such sensor-based systems including the interfacing between sensor devices and other components within the system. As an example, the interface between a sensor and a processor device can be difficult and challenging to design for a number of reasons. Many prior art devices require access to relatively high power or voltage levels to perform properly. The prior art devices do not provide adequate solutions to address applications that operate in relatively lower power or lower voltage situations. Also, certain prior art devices also are implemented using semiconductor fabrication process technology that results in devices having relatively large die size. Such prior art devices can be relatively expensive in terms of cost and consumptive in terms of size and real estate.

While a great deal of effort has been focused to address these and other challenges, there still remains a great deal of room for improvement of individual devices within sensor-based systems including sensors themselves, the interfaces between sensors and other devices, etc.

BRIEF DESCRIPTION OF THE SEVERAL VIEWS OF THE DRAWINGS

FIG. 1A is a diagram illustrating an embodiment of one or more communication systems that includes a sensor interface.

FIG. 1B is a diagram illustrating another embodiment of one or more communication systems that includes a sensor interface.

FIG. 1C is a diagram illustrating another embodiment of one or more communication systems that includes a sensor interface.

FIG. 3A is a diagram illustrating an example of a sensor interface.

FIG. 3B is a diagram illustrating another example of a sensor interface.

FIG. 5A is a diagram illustrating another example of a sensor interface.

FIG. 5B is a diagram illustrating another example of a sensor interface.

DETAILED DESCRIPTION

Figure 2A:
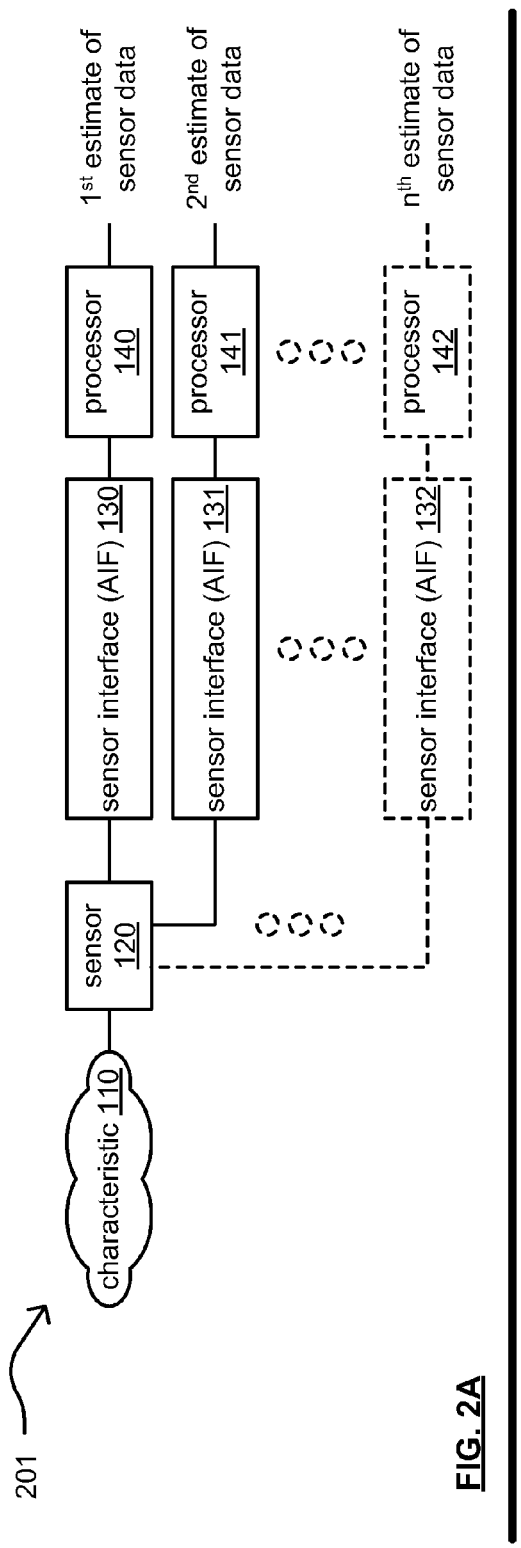
FIG. 2A is a diagram illustrating another embodiment of one or more communication systems that includes a sensor interface.

FIG. 1A is a diagram illustrating an embodiment 101 of one or more communication systems that includes a sensor interface. This disclosure presents various novel solutions for sensor interfaces and other components within sensor-based systems. The various embodiments and examples presented herein may be implemented within a wide variety of applications including those implemented in a general sensing environment. There are many examples of sensing environments and sensor-based systems. Some examples include those sensor-based systems directed towards applications within any one of biomedical, environmental, security, processing, manufacturing, operational, etc. applications. Generally speaking, the various architectures and designs presented in this disclosure may be adapted and applied to any desired sensor-based system. Some examples of environmental characteristics include temperature, humidity, barometric pressure, etc. Some examples of biomedical characteristics include body temperature, heart rate, respiratory rate, blood pressure, etc. Note that such examples of such characteristics are not exhaustive. Generally, one or more sensors are implemented within the system to monitor or detect one or more characteristics.

In this embodiment 101, a sensor 120 detects or monitors a characteristic 110 and generates a sensor signal based thereon. The sensor signal may be an electrical signal, such as a voltage or current signal. The sensor 120 provides the sensor signal to a sensor interface 130. The sensor interface 130 may be viewed as being an analog interface (AIF) that generates a digital signal that is provided to processor 140 that generates an estimate of the sensor data within the sensor signal as generated by the sensor 120.

In one example implementation, the sensor interface 130 includes an on-chip clock generation circuit that obviates any need for an externally provided highly accurate clock signal. This clock generation circuit generates the one or more clock signals used by the various components within the sensor interface 130. In such an example, the on-chip clock generation circuit includes an on-chip relaxation oscillator circuit and a digital phase locked loop (PLL) that operate cooperatively to generate a highly accurate clock signal on-chip. Also, the sensor interface 130 includes functionality to perform an electrical to optical to electrical conversion. For example, a light source (e.g., a emitting diode (LED)) generates an optical signal based on a sensor signal that is generated by the sensor 120. The optical signal is then representative of the sensor signal that is representative of the characteristic 110 that is being monitored or detected. Subsequently, a light detection device (e.g., a photodiode (PD)) generates an electrical signal (e.g., a current signal) based on the optical signal provided from the light source. The sensor interface 130 also includes an analog to digital converter (ADC) that generates a digital signal based on the electrical signal provided by the light detection device. This ADC operates based on a clock signal generated by the clock generation circuit.

A processor within the sensor interface 130 processes the digital signal estimate of the sensor data within the sensor signal to monitor or detect the characteristic 110. An amplifier is implemented between the photodiode and the ADC to process the current signal generated by the light detection device before it is provided to the ADC. This amplifier may also operate based on a feedback current signal generated by a current digital to analog converter (CDAC) that is implemented within a feedback loop that receives as its input the digital signal generated by the ADC. This CDAC also operates based on a clock signal generated by the clock generation circuit. When operating by using the current signal provided by the photodiode and the feedback current signal, the amplifier will operate with reduced noise sensitivity. In situations in which relatively small signals are being detected, a reduction in noise sensitivity will improve the sensor interface's operation. Note also, in some examples, more than one feedback current signal is provided to the amplifier. A first current feedback signal may be generated using a first CDAC that operates based on the digital signal generated by the ADC, and a second current feedback signal may be generated using a second CDAC that operates based on a static control signal.

As shown within FIG. 1A, a singular sensor 120 monitors and detects a single characteristic 110 and provides a sensor signal to sensor interface 130 that generates a digital signal that is provided to processor 140 that generates an estimate of sensor data that is based on the characteristic 110. Several other diagrams are provided and show various permutations and examples in which different numbers of characteristics may be monitored and detected using different numbers of sensors, sensor interfaces, processors, etc.

FIG. 1B is a diagram illustrating another embodiment 102 of one or more communication systems that includes a sensor interface. In this diagram, a number of characteristics 110, 111, through 112 are monitored or detected by respective sensors 120, 121, through 122. Each respective sensor provides a sensor signal to a corresponding sensor interface. For example, sensor 120 provides a first sensor signal to sensor interface 130, sensor 121 provides a second sensor signal to sensor interface 131, and so on. Each respective sensor interface provides a digital signal to a respective processor. Sensor interface 130 provides a first digital signal to processor 140 that generates an estimate of first sensor data associated with characteristic 110. Sensor interface 131 provides a second digital signal to processor 141 that generates an estimate of second sensor data associated with characteristic 111. Generally speaking, any number of characteristics up to characteristic 112, any number of sensors up to sensor 122, any number of sensor interfaces up to sensor interface 132, and any number of processors up to processor 142 may be implemented within a given configuration. This embodiment 102 shows multiple respective paths between characteristic and processor.

FIG. 1C is a diagram illustrating another embodiment 103 of one or more communication systems that includes a sensor interface. In this diagram, two or more sensors 120-122 monitor or detect two or more characteristics 110-112, and two or more sensor interfaces 130-132 operate to generate respective digital signals based on the characteristics 110-112. A singular processor 140 receives the number of digital signals to generate estimates of sensor data associated with the characteristics 110-112.

FIG. 2A is a diagram illustrating another embodiment 201 of one or more communication systems that includes a sensor interface. In this diagram, a number of sensor interfaces 130-132 each receive a sensor signal from sensor 120 that monitors and detects characteristic 110. Different sensor interfaces may be implemented differently by including different elements, components, processing devices, filters, analog to digital converters (ADCs), feedback loops, etc. There may be instances in which different sensor interfaces are used to generate different digital signals based on the same sensor signal provided from a common sensor 120. In this diagram, different processors 140-142 each respectively operate on the different digital signals provided from the sensor interfaces 130-132 to generate different estimates of the sensor data associated with the characteristic 110. In other words, each of the respective processors 140-142 generates a different estimate of the sensor data based on the sensor signal or information provided from the sensor 120 via the different sensor interfaces 130-132.

Figure 2B:
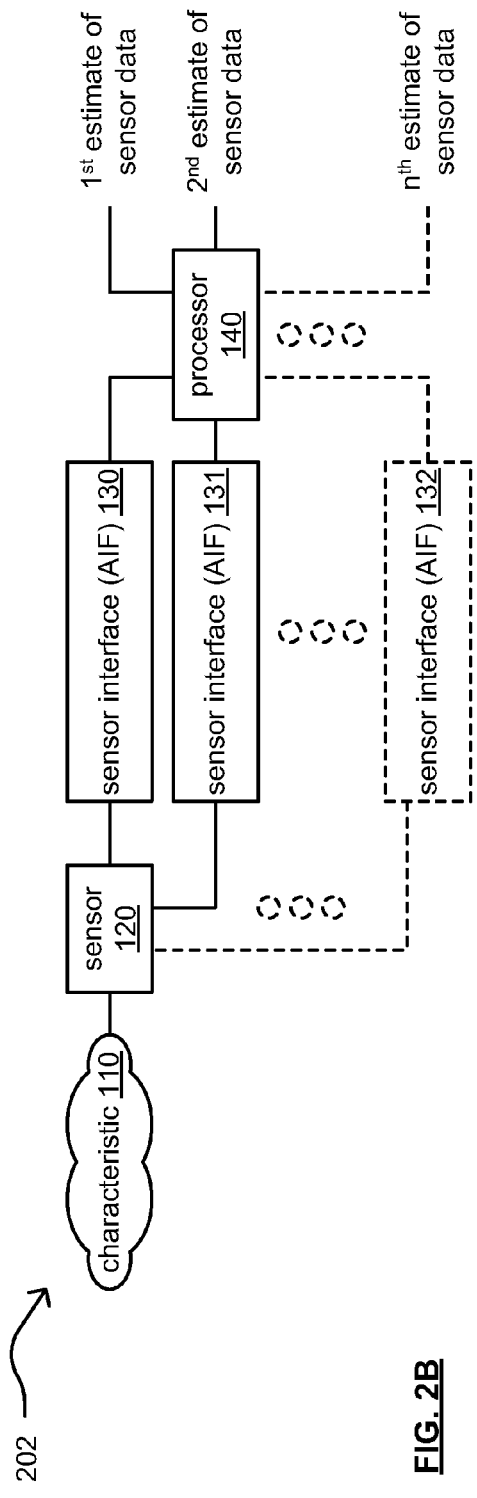
FIG. 2B is a diagram illustrating another embodiment of one or more communication systems that includes a sensor interface.

FIG. 2B is a diagram illustrating another embodiment 202 of one or more communication systems that includes a sensor interface. The embodiment 202 of this diagram is similar to the embodiment 201 of the previous diagram with the exception that a single processor 140 receives the digital signals provided from the sensor interfaces 130-132. In this diagram, a single processor 140 may then differentiate characteristics between the different digital signals provided via different sensor interfaces based on knowledge of the particular architecture and design of the different sensors. If desired, the processor 140 may select among and use different digital signals provided from the different sensor interfaces 130-132 based on any consideration. For example, in certain instances, a digital signal provided by one of the sensor interfaces 130-132 may be preferable over another digital signal provided by another one of the sensor interfaces 130-132. There may be instances in which different sensor interfaces generate digital signals based on the same or a common sensor signal differently based on their respective different components, architectures, etc.

FIG. 3A is a diagram illustrating an example 301 of a sensor interface. A sensor input is provided to a transducer that generates a sensor signal. This transducer may be viewed as being implemented within a sensor that monitors or detects a characteristic and generates the sensor signal based thereon. For example, the transducer will be appropriately tailored to deal with the type of characteristic that it detects or monitors. The sensor signal will then be an electrical signal that corresponds to the sensor input and that is capable to drive a light source, such as a light emitting diode (LED). The LED then generates an optical signal based on the sensor signal. Note that the optical signal is representative of the sensor signal provided to the LED. A photodiode (PD) generates a first current signal based on the optical signal provided by the LED. An amplifier generates a second current signal based on the first current signal and the feedback current signal. An analog to digital converter (ADC) digitally samples the second current signal output from the amplifier to generate a digital signal. In this example 301, this digital signal is also provided to a current digital to analog converter (CDAC) that generates an updated feedback signal that is added to the first current signal output from the photodiode and input to the amplifier. This feedback loop provided by the CDAC reduces noise sensitivity of the amplifier and improves its performance. Processor 140 operates on the digital signal to estimate sensor data within the sensor signal provided from the transducer to the LED. If desired, a decimation filter and a first-in first-out (FIFO) buffer may further process the digital signal output from the ADC before undergoing processing by the processor 140.

In addition, this example 301 of the sensor interface also includes a clock generation circuit. The clock generation circuit includes an oscillator circuit that generates a first clock signal and a phase locked loop (PLL) (e.g., a digital PLL) that generates a second clock signal that is synchronized to the first clock signal and based on the first clock signal. The second clock signal may include a different frequency than the first clock signal and/or a different phase, offset, etc. relative to the first clock signal. Such an architecture allows for different clock signals having different characteristics to be generated locally and used for various purposes within the sensor interface. For example, both the ADC and CDAC of this sensor interface operate based on a clock signal generated by the clock generation circuit. In some instances, the ADC and CDAC of this sensor interface operate based on different clock signals that are both generated by the clock generation circuit.

FIG. 3B is a diagram illustrating another example 302 of a sensor interface. The front end of this interface is similar to the prior example 301 of FIG. 3A. However, the current signal output from the photodiode (which may be the same current signal output from the photodiode of the prior example 301 or a different current signal if a different front end is included within this example 302) is provided to a low noise amplifier (LNA) that generates a first differential signal. An anti-aliasing (AA) filter generates a second differential signal based on the first differential signal after having filtered the first differential signal. An analog to digital converter (ADC) digitally samples the second differential signal to generate a digital signal based on the sensor signal provided from the transducer. This ADC may be a second order switched capacitor (SC) sigma-delta ($\Sigma\Delta$) design in certain examples. This example 302 also includes a clock generation circuit, and the ADC operates based on a clock signal that is generated by the clock generation circuit. Processor 140 operates on the digital signal to estimate sensor data within the sensor signal provided from the transducer to the LED.

Figure 4:
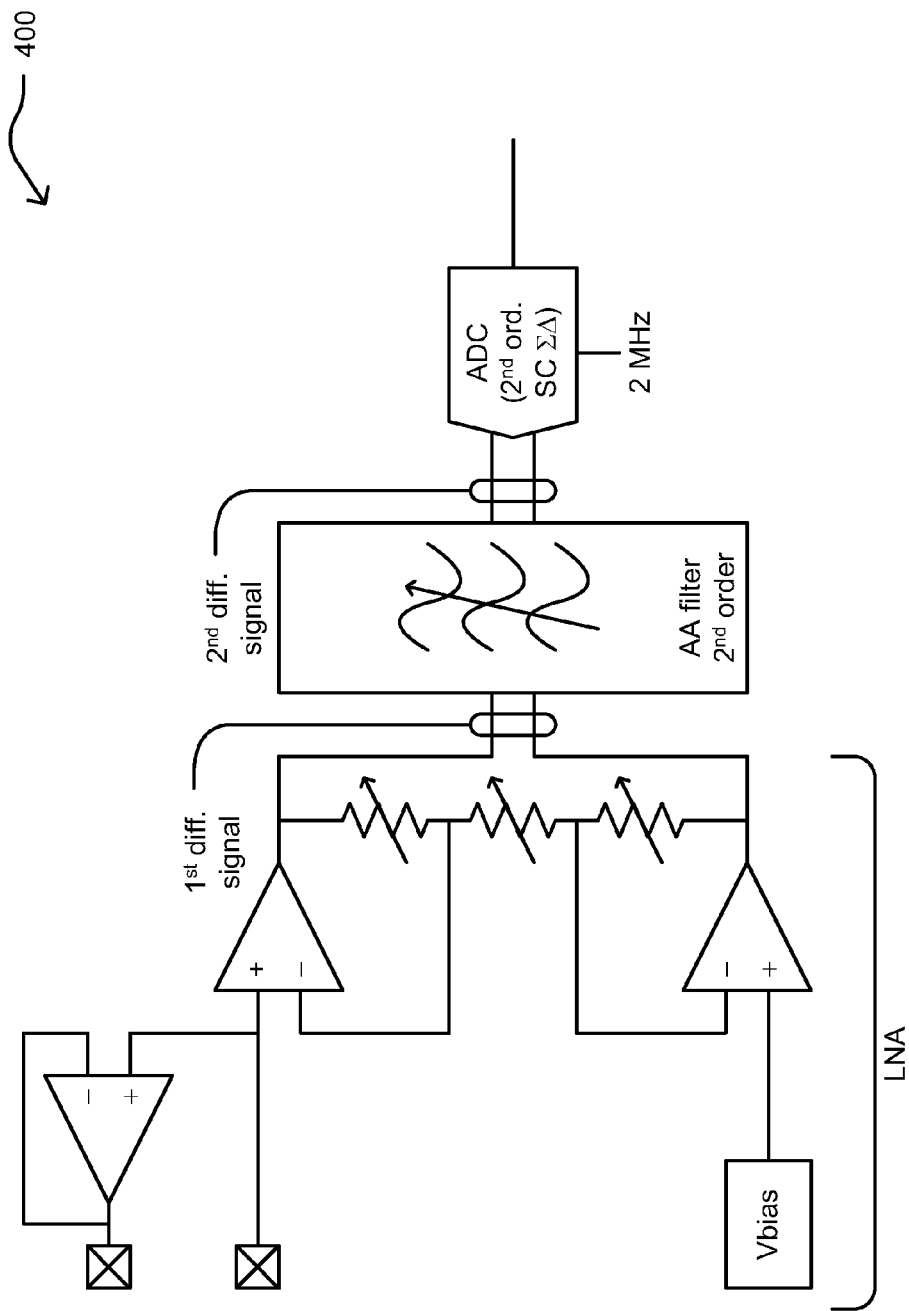
FIG. 4 is a diagram illustrating another example of a sensor interface.

FIG. 4 is a diagram illustrating another example 400 of a sensor interface. A low noise amplifier (LNA) is implemented using the dual stage amplifier configuration. The amplifiers may be implemented using a transistor pair configuration such as using MOSFET transistors. An input current signal (e.g., such as provided from a photodiode) is provided to the non-inverting input of the top amplifier via a pad or contact that is shown as a square with an X therein. If desired, the same input current signal may be provided to another amplifier shown at the top left of the diagram to generate another type of the input current signal for other uses within the sensor interface or another element or component within the system. A voltage bias is provided to the amplifier shown at the bottom of the diagram. The dual stage amplifier generates a first differential signal that is provided to an anti-aliasing (AA) filter that generates a second differential signal. An analog to digital converter (ADC) digitally samples the second differential signal output from the AA filter to generate a digital signal based on the sensor signal provided from the transducer. This ADC may be a second order switched capacitor (SC) sigma-delta ($\Sigma\alpha$) design in certain examples. This ADC may operate to perform sampling of the second differential signal using a clock signal having a frequency of 2 MHz as provided by an on-chip clock generation circuit.

A sensor interface constructed using this architecture is very robust using such components as an LNA, and AA filter, and an ADC. Certain circuit level optimizations in this design allow for low-power consumption. For example, if desired, the LNA, the AA filter, and a first integrator may all be implemented within the ADC itself thereby providing a highly integrated architecture having low-power consumption.

FIG. 5A is a diagram illustrating another example 501 of a sensor interface. The photodiode provides a current signal to an amplifier having a feedback capacitor and having one of its inputs biased using a voltage reference (e.g., VREF =1.5 V). An ADC digitally samples the current signal output from the amplifier to generate a digital signal that is provided to a decimation filter and also fed back to a CDAC to generate a feedback current signal that is summed with the current signal provided from the photodiode and then input to the amplifier. Both the ADC and CDAC of this sensor interface operate based on a clock signal (CLK 2) that is generated using an on-chip clock generation circuit.

The feedback loop provided by the CDAC will reduce noise sensitivity of the ADC and the sensor interface in general. For example, a design constraint may be that the CDAC noise should be less than 20 pico-Amps (pA) within a desired frequency range. For example, the use of such a feedback loop can operate to improve the overall performance of the sensor interface. Appropriately tuned operation of the feedback loop can reduce any noise in the current signal that is provided to the amplifier. In an example of operation, an 84micro-amps ($\mu$A) full-scale current and VREF =1.5 V includes a corresponding resistance required to generate the current of 17.9 kilo-Ohms (k$\Omega$). This provides a 4KT/R current noise below 78 pico-Amps (pA) within a bandwidth of 6.6 kHz. In addition, when a relatively small amount of feedback current is enabled (e.g., Idc =5 micro-amps ($\mu$A)), then the noise in the current signal may be reduced even further (e.g., below 19 pA within a bandwidth of 6.6 kHz with a corresponding resistance required to generate the current of 300 k$\Omega$). Additional design variations may be made such as increasing the voltage reference level (e.g., increase VREF =3 V or 2.8 V). In this instance, noise in the current signal may be reduced even further (e.g., below 13.8 pA within a bandwidth of 6.6 kHz with a corresponding resistance required to generate the current of 560 k$\Omega$)

FIG. 5B is a diagram illustrating another example 502 of a sensor interface. This diagram shows a similar architecture to the prior diagram with the addition of a dynamic element match component that is implemented between the output of the ADC and the input of the CDAC as well as a calibrated static CDAC that operates based on a static control signal provided thereto. The value of the static control signal provided to the calibrated static CDAC may be determined in a prior startup process. Such a design allows for a reduction in the full-scale range of the sigma-delta ($\Sigma\Delta$) modulator loop, and also reduces noise sensitivity of the CDAC that is driven using the digital signal output from the ADC after having been passed through the dynamic element match component. This design architecture allows for an increase in the integrator gain along with a reduction in sensitivity to ADC noise.

Note that other design examples may exclude the feedback loop of the CDAC and/or calibrated static CDAC provided within examples 501 in 502 in FIG. 5A and FIG. 5B.

Figure 6A:
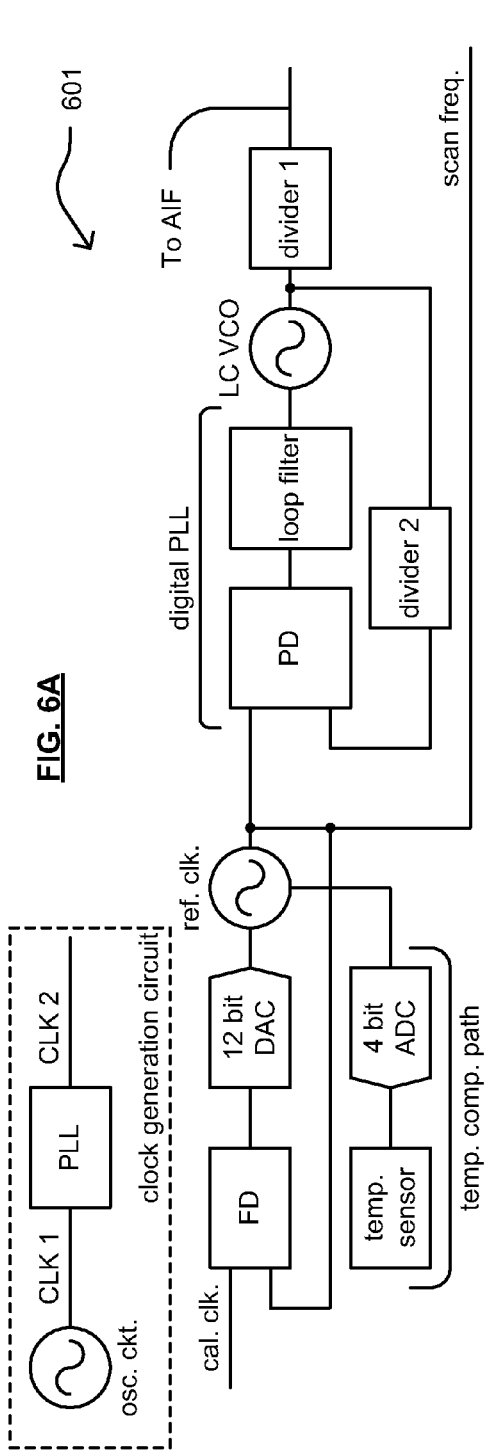
FIG. 6A is a diagram illustrating an example of a clock generation circuit.

FIG. 6A is a diagram illustrating an example 601 of a clock generation circuit. This clock generation circuit includes an on-chip relaxation oscillator circuit shown on the left-hand side of the diagram and a digital phase locked loop (PLL) shown on the right hand side of the diagram. The on-chip relaxation oscillator circuit may be implemented using a resistor capacitor (RC) oscillator that includes a resistor-capacitor resonant circuit, an inductor capacitor (LC) oscillator that includes an inductor-capacitor resonant circuit, or other architecture using relatively inexpensive components. The combination of an on-chip relaxation oscillator circuit and a digital PLL allows for the generation of clock signals on-chip and obviates the need for a highly accurate and expensive crystal or clock reference. In addition, because the clock signals are generated on-chip, there is no need to interface with another device that provides relatively highly accurate clock signals. Such an architecture also allows for relatively low power consumption when compared to designs that include highly accurate and often high-powered clock generation architectures.

The on-chip relaxation oscillator circuit generates a first clock signal shown as ref. clk. If desired, a one-time calibration process may be performed by a feedback loop implemented using a digital frequency locked loop (FLL) to process the first clock signal in conjunction with a highly accurate calibration clock (e.g., cal. clk., which may be provided from on-chip for this one-time calibration process). The highly accurate calibration clock and the first clock signal are provided to a frequency detector (FD) and the difference is provided to a 12 bit DAC whose output adjusts the on-chip relaxation oscillator circuit to adjust the first clock signal based on this one-time calibration process. In an example of calibration, one point calibration may be performed per chip and 27°. The one point calibration uses a digital FLL whose reference is the highly accurate calibration clock that may be provided from on-chip for the one time calibration process. The 12 bit DAC (e.g., a CDAC) used in the digital FLL blocks the internal oscillator (e.g., ref. clk.) to the highly accurate calibration clock to ensure that process variation is calibrated out between different chips.

In addition, if desired, temperature compensation path may also be included to guarantee accuracy of the first clock signal over a desired temperature range (e.g., 500 ppm accuracy over some selected temperature range). In an example of temperature calibration, background temperature calibration is performed on-chip using an integrated temperature sensor and a 4 bit ADC to calibrate out temperature variability in the design.

This first clock signal is provided to the digital PLL that includes a phase detector (PD), loop filter (LF), another oscillator (e.g., an LC voltage controlled oscillator (VCO)), and a divider (divider 2) in a feedback loop to provide another input to the PD. Another divider (divider 1) processes the second clock signal (e.g., CLK 2) that is generated by the digital PLL that is provided to one or more sensor interfaces (or AIFs) for use by one or more components therein (e.g., DAC, CDAC, etc.). The selection of an LC VCO may be made based on its relatively superior phase noise and reduced jitter when compared to other oscillator designs (e.g., such as when compared to RC oscillator designs). For example, such an LC VCO may be designed to have less than approximately 100 pico-seconds (ps) RMS jitter, be implemented in silicon having an area of approximately 0.4 mm², and a current consumption of approximately 600 μA from typical corner.

Figure 6B:
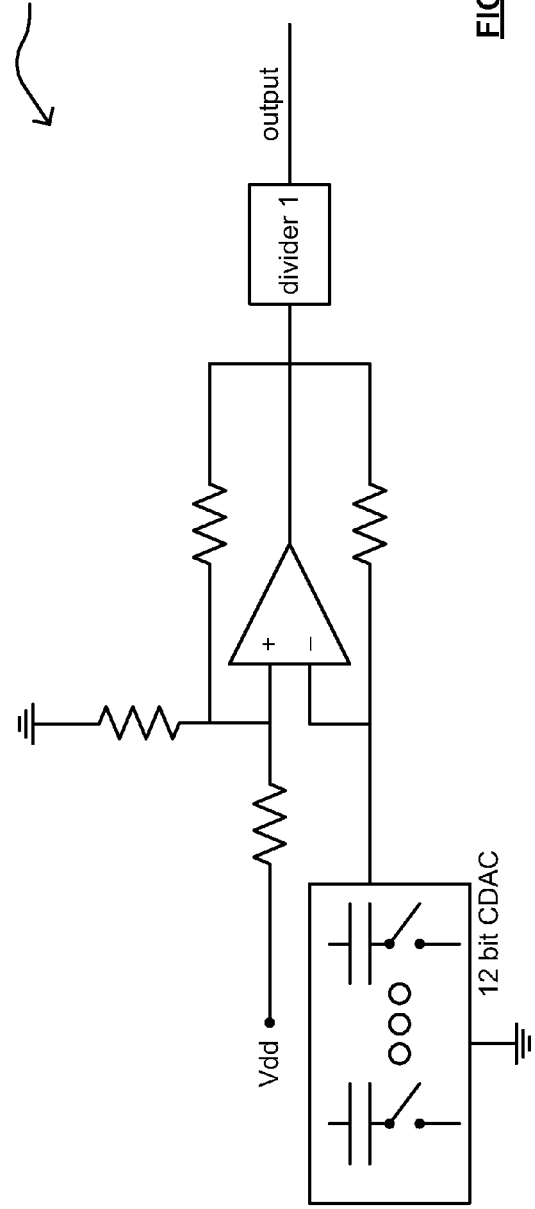
FIG. 6B is a diagram illustrating an example of an on-chip relaxation oscillator circuit that may be implemented within a clock generation circuit.

FIG. 6B is a diagram illustrating an example 602 of an on-chip relaxation oscillator circuit that may be implemented within a clock generation circuit. This example of an on-chip relaxation oscillator circuit may be included within the clock generation circuit of example 601 in FIG. 6A. Appropriate control of the switches within the 12 bit CDAC allow for generation of the first clock signal at a desired frequency.

Figure 7:
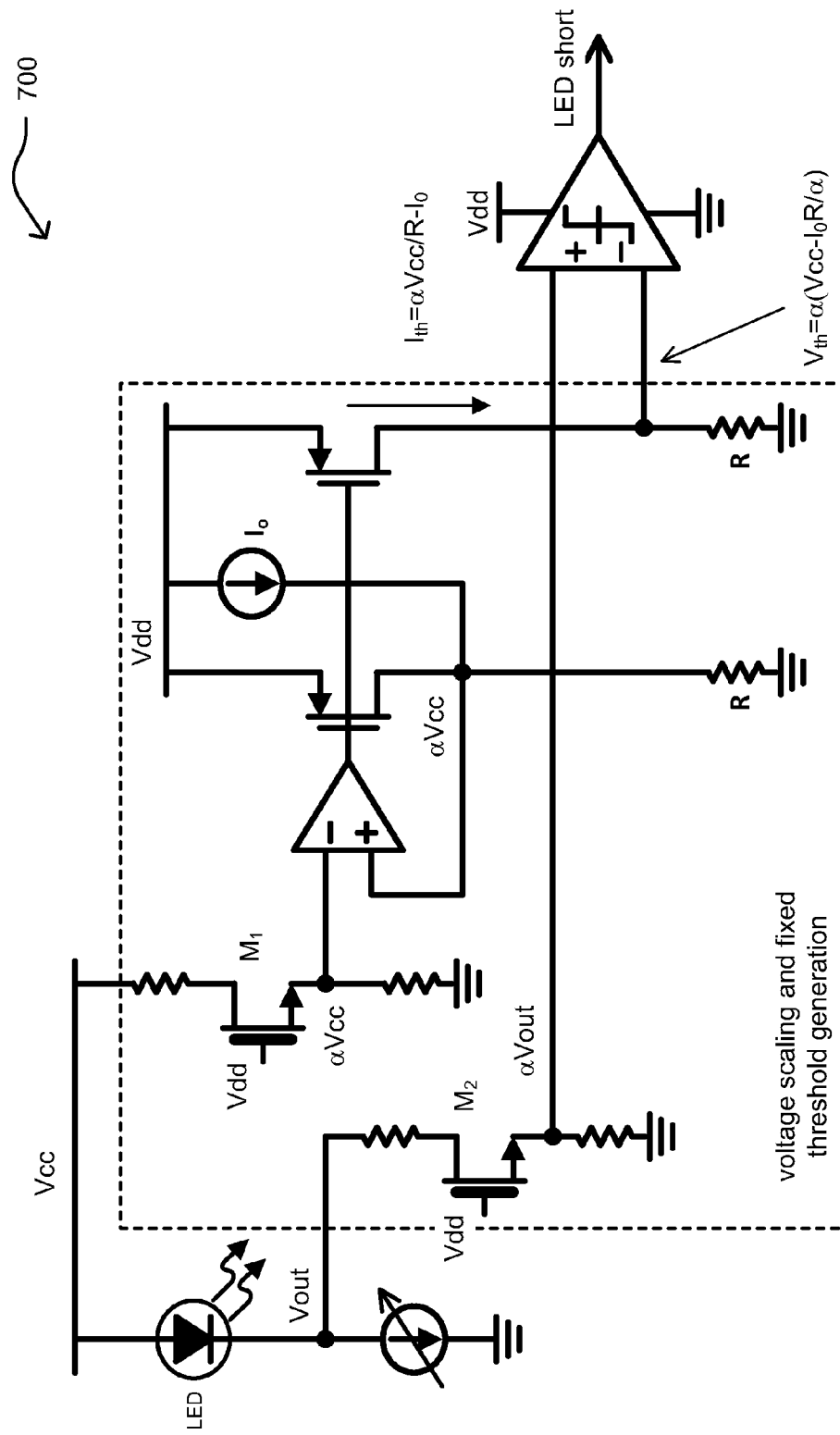
FIG. 7 is a diagram illustrating an example of a light emitting diode (LED) short detection circuit.

FIG. 7 is a diagram illustrating an example 700 of a light emitting diode (LED) short detection circuit. Operation of such a LED short detection circuit can fail for implementations that have a large variation of supply voltage. A large varying supply voltage may be required for proper LED operation. While certain prior art LED short detection circuits cannot cover broad ranges of voltage supply variation, this architecture can accommodate a broad range of voltage supplies and voltage supply variations. Also, a relatively large glitch in voltage supply may be introduced when the LED fires, and such a glitch can cause a false detection in prior art designs. In addition, prior art designs will not operate properly when the voltage supply variation of the LED exceeds the reliable and predictable voltage range required for nominal transistor operation. As such, certain prior art designs include a large area, high-voltage transistor to protect the overall LED short detection circuit in such situations. This novel LED short detection circuit addresses these deficiencies and generates a scaled version of the voltage detection threshold for use at the input to the comparator on the right hand side of the diagram such that $\alpha(Vcc-V_{fix}) < \alpha V_{out}$, where is $V_{out}$ the output voltage, $\alpha$ is the scale factor, and Vcc is the voltage supply provided to the LED. The Vcc value is scaled by $\alpha$ and then subtraction is performed in the current domain. Subsequently, conversion is made back to the voltage domain and compared with $\alpha V_{out}$.

As shown in the diagram, this example 700 of a LED short circuit detection circuit that includes a first resistor array configured to scale a voltage supply connected to a first node of the LED (Vcc) to generate a first scaled voltage ($\alpha V_{out}$). It also includes a second resistor array configured to scale an output voltage provided from a second node of the LED to generate a second scaled voltage ($\alpha$Vcc). This second scale voltage ($\alpha$Vcc) is provided to a threshold circuit that scales the second scaled voltage ($\alpha$Vcc) to generate a threshold voltage ($V_{th}$). This ($\alpha$Vcc) generates the threshold current, $I_{th}$, which is used to generate the threshold voltage, $V_{th}$, as follows:

$$I_{th} = (\alpha Vcc/R) - I_0, \text{ where}$$

$$V_{th} = I_{th}R = \alpha(Vcc - (I_0 R/\alpha))$$

A comparator generates an LED short signal based on the first scaled voltage ($\alpha V_{out}$) and the threshold voltage ($V_{th}$). This LED short signal represents a value of zero within the first optical signal. The LED short circuit threshold is then, $V_{fix}$, which is represented as $I_0 R/\alpha$.

As performed in this architecture, the voltage scaling of Vcc and $V_{out}$ are done with resistor arrays. By implementing subtraction in current domain, LED short circuit detection is done by comparing $\alpha V_{out}$ and $\alpha(Vcc-V_{fix})$, where $V_{fix} = I_0 R/\alpha$. LED short circuit threshold $V_{fix}$ is internally generated bandgap voltage, independent of supply voltage. This design includes two small high-voltage devices $M_1$ and $M_2$ (e.g., MOSFET transistors) for over-voltage protection. The remaining components, elements, and circuits can operate at a much lower supply voltage than Vcc (e.g., they can operate at a lower supply voltage of Vdd). This design provides for supply independent LED short circuit detection threshold while using only a very small number of high-voltage devices that are needed and provide for reduced circuit complexity. This also allows for detection of short circuits in LEDs with a much broader range of colors than prior art techniques while also allowing tolerance for a more tolerable and/or wider range of supply voltages. In production, this will allow for lower cost with smaller number of area expensive high-voltage devices.

Figure 8:
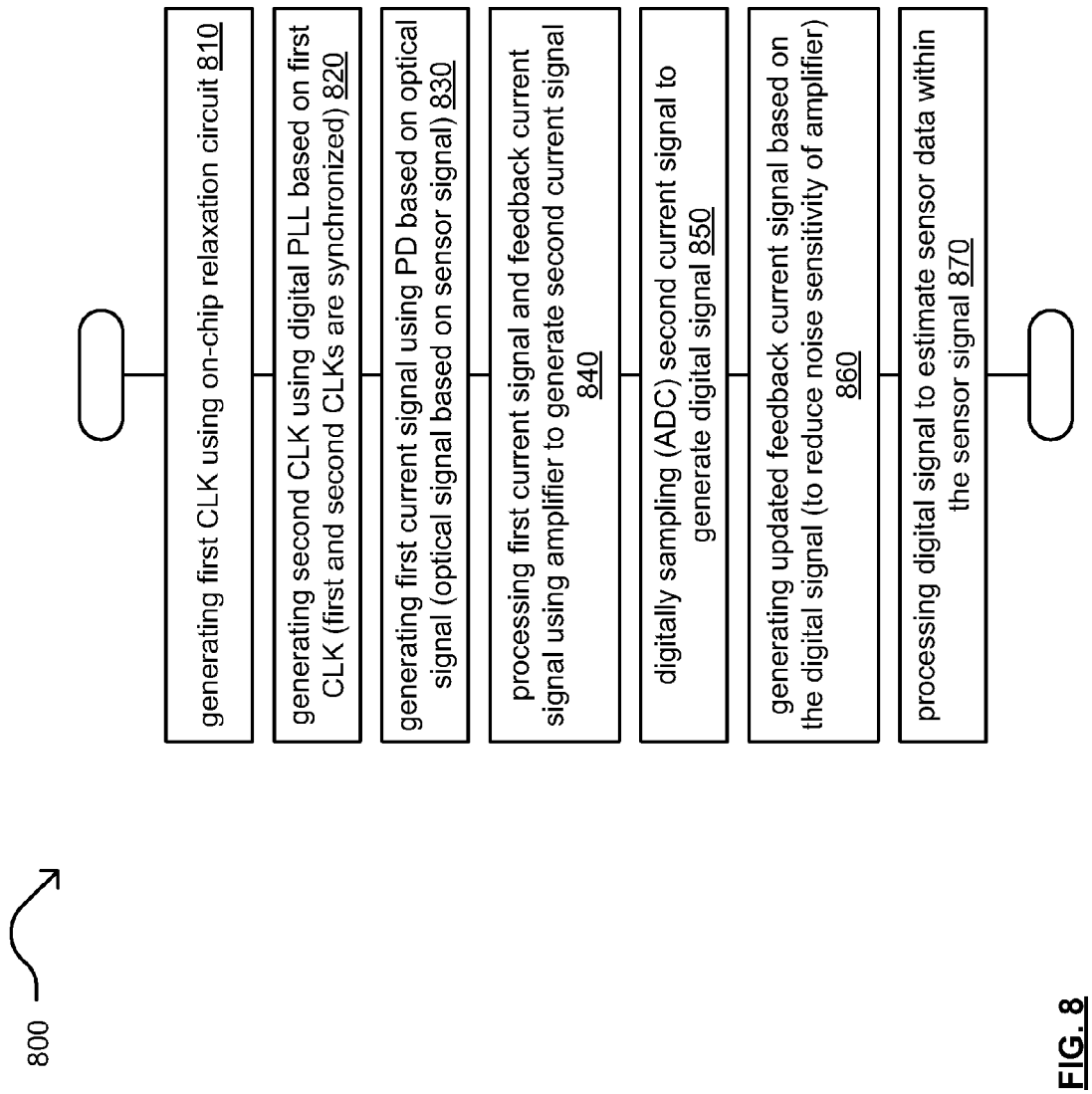
FIG. 8 is a diagram illustrating an embodiment of a method for execution by a sensor device.

FIG. 8 is a diagram illustrating an embodiment of a method 800 for execution by a sensor device.

The method 800 begins by generating a first clock signal using an on-chip relaxation oscillator circuit (block 810). The method 800 continues by generating a second clock signal using a digital phase locked loop (PLL) and based on the first clock signal (block 820). The second clock signal may be designed to be synchronized to the first clock signal. The method 800 then continues by operating a photodiode configured to generate a first current signal based on an optical signal (block 830). The optical signal is representative of a sensor signal.

The method 800 continues by generating a second current signal using an amplifier that operates based on the first current signal and a feedback current signal (block 840). The method 800 continues by digitally sampling the second current signal using an analog to digital converter (ADC) that operates based on the second clock signal to generate a digital signal (block 850).

The method 800 then operates by generating an updated feedback current signal based on the digital signal (e.g., by operating a current digital to analog converter (CDAC) that operates based on the second clock signal) (block 860). The updated feedback current signal reduces noise sensitivity of the amplifier. The method 800 continues by processing the digital signal to estimate sensor data within the sensor signal (block 870).

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "configured to," "operably coupled to," "coupled to," and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "configured to," "operable to," "coupled to," or "operably coupled to" indicates that an item includes one or more of power connections, input(s), output(s), etc., to perform, when activated, one or more its corresponding functions and may further include inferred coupling to one or more other items. As may still further be used herein, the term "associated with," includes direct and/or indirect coupling of separate items and/or one item being embedded within another item.

As may be used herein, the term "compares favorably" or equivalent, indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

As may also be used herein, the terms "processing module," "processing circuit," "processor," and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures. Such a memory device or memory element can be included in an article of manufacture.

One or more embodiments of an invention have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention. One of average skill in the art will also recognize that the functional building blocks, and other illustrative blocks, modules and components herein, can be implemented as illustrated or by discrete components, application specific integrated circuits, processors executing appropriate software and the like or any combination thereof.

The one or more embodiments are used herein to illustrate one or more aspects, one or more features, one or more concepts, and/or one or more examples of the invention. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

Note that many of the various amplifiers, circuits, elements, components, etc. described herein and in the above described figure(s) may be implemented using transistors such as field effect transistors (FETs). As one of ordinary skill in the art will appreciate, the transistors may be implemented using any type of transistor structure including, but not limited to, bipolar, metal oxide semiconductor field effect transistors (MOSFET), N-well transistors, P-well transistors, enhancement mode, depletion mode, and zero voltage threshold (VT) transistors.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module includes a processing module, a processor, a functional block, hardware, and/or memory that stores operational instructions for performing one or more functions as may be described herein. Note that, if the module is implemented via hardware, the hardware may operate independently and/or in conjunction with software and/or firmware. As also used herein, a module may contain one or more sub-modules, each of which may be one or more modules.

While particular combinations of various functions and features of the one or more embodiments have been expressly described herein, other combinations of these features and functions are likewise possible. The present disclosure of an invention is not limited by the particular examples disclosed herein and expressly incorporates these other combinations.

What is claimed is:

1. A sensor interface comprising:
   an on-chip relaxation oscillator circuit configured to generate a first clock signal;
   a digital phase locked loop (PLL) configured to generate a second clock signal based on the first clock signal, wherein the second clock signal is synchronized to the first clock signal;
   a photodiode configured to generate a first current signal based on an optical signal, wherein the optical signal is representative of a sensor signal;
   an amplifier configured to generate a second current signal based on the first current signal and a feedback current signal;
   an analog to digital converter (ADC) configured to operate based on the second clock signal and to generate a digital signal based on the second current signal;
   a current digital to analog converter (CDAC) configured to operate based on the second clock signal and to generate an updated feedback current signal based on the digital signal, wherein the updated feedback current signal reduces noise sensitivity of the amplifier; and
   a processor configured to process the digital signal to estimate sensor data within the sensor signal.

2. The sensor interface of claim 1 further comprising:
   another CDAC that includes a calibrated static CDAC configured to generate another feedback current signal based on a static control signal; and
   an adder configured to add the another feedback current signal to the updated feedback current signal to reduce the noise sensitivity of the amplifier.

3. The sensor interface of claim 1 further comprising:
   a transducer configured to generate the sensor signal based on a sensor input; and
   a light emitting diode (LED) light source configured to generate the optical signal based on the sensor signal; and
   an LED short circuit detection circuit that includes:
     a first resistor array configured to scale a voltage supply connected to a first node of the LED to generate a first scaled voltage;
     a second resistor array configured to scale an output voltage provided from a second node of the LED to generate a second scaled voltage;
     a threshold circuit configured to scale the second scaled voltage to generate a threshold voltage; and
     a comparator configured to generate an LED short signal based on the first scaled voltage and the threshold voltage, wherein the LED short signal represents a value of zero within the optical signal.

4. The sensor interface of claim 3, wherein the sensor input is representative of an environmental characteristic that corresponds to:
   temperature;
   humidity; or
   barometric pressure.

5. The sensor interface of claim 3, wherein the sensor input is representative of a biomedical characteristic that corresponds to:
   body temperature;
   heart rate;
   respiratory rate; or
   blood pressure.

6. The sensor interface of claim 1, wherein the on-chip relaxation oscillator circuit includes an RC oscillator that includes a resistor-capacitor resonant circuit or an LC oscillator that includes an inductor-capacitor resonant circuit.

7. The sensor interface of claim 1, wherein the on-chip relaxation oscillator circuit includes a temperature sensor configured to calibrate the first clock signal based on change of environmental temperature.

8. The sensor interface of claim 1 further comprising:
a low noise amplifier (LNA) to generate a first differential signal based on the first current signal or a third current signal that is representative of another sensor signal;
an anti-aliasing filter configured to generate a second differential signal based on the first differential signal;
another ADC configured to operate based on the second clock signal and to generate another digital signal based on the second differential signal; and
the processor configured to process the another digital signal to estimate the sensor data within the sensor signal or to estimate other sensor data within the another sensor signal.

9. A sensor interface comprising:
an on-chip relaxation oscillator circuit configured to generate a first clock signal;
a digital phase locked loop (PLL) configured to generate a second clock signal based on the first clock signal, wherein the second clock signal is synchronized to the first clock signal;
a first analog interface that includes:
  a first photodiode configured to generate a first current signal based on a first optical signal, wherein the first optical signal is representative of a first sensor signal;
  a first amplifier configured to generate a second current signal based on the first current signal and a feedback current signal; and
  a first analog to digital converter (ADC) configured to operate based on the second clock signal and to generate a first digital signal based on the second current signal; and
  a current digital to analog converter (CDAC) configured to operate based on the second clock signal and to generate an updated feedback current signal based on the first digital signal, wherein the updated feedback current signal reduces noise sensitivity of the first amplifier; and
a second analog interface that includes:
  a second photodiode configured to generate a third current signal based on a second optical signal, wherein the second optical signal is representative of a second sensor signal;
  a low noise amplifier (LNA) to generate a first differential signal based on the third current signal that is representative of the second sensor signal;
  an anti-aliasing filter configured to generate a second differential signal based on the first differential signal;
  another ADC configured to operate based on the second clock signal and to generate a second digital signal based on the second differential signal; and
a processor configured to:
  process the first digital signal to estimate first sensor data within the first sensor signal; and
  process the second digital signal to estimate second sensor data within the second sensor signal.

10. The sensor interface of claim 9 further comprising:
a transducer configured to generate the first sensor signal based on a sensor input; and
a light emitting diode (LED) light source configured to generate the first optical signal based on the first sensor signal; and
an LED short circuit detection circuit that includes:
  a first resistor array configured to scale a voltage supply connected to a first node of the LED to generate a first scaled voltage;
  a second resistor array configured to scale an output voltage provided from a second node of the LED to generate a second scaled voltage;
  a threshold circuit configured to scale the second scaled voltage to generate a threshold voltage; and
  a comparator configured to generate an LED short signal based on the first scaled voltage and the threshold voltage, wherein the LED short signal represents a value of zero within the first optical signal.

11. The sensor interface of claim 9, wherein the first analog interface further comprises:
another CDAC that includes a calibrated static CDAC configured to generate another feedback current signal based on a static control signal; and
an adder configured to add the another feedback current signal to the updated feedback current signal to reduce the noise sensitivity of the first amplifier.

12. The sensor interface of claim 9, wherein the first sensor signal or the second sensor signal is representative of an environmental characteristic that corresponds to:
temperature;
humidity; or
barometric pressure.

13. The sensor interface of claim 9, wherein the first sensor signal or the second sensor signal is representative of a biomedical characteristic that corresponds to:
body temperature;
heart rate;
respiratory rate; or
blood pressure.

14. A method for execution by a sensor device, the method comprising:
generating a first clock signal using an on-chip relaxation oscillator circuit;
generating a second clock signal using a digital phase locked loop (PLL) and based on the first clock signal, wherein the second clock signal is synchronized to the first clock signal;
operating a photodiode configured to generate a first current signal based on an optical signal, wherein the optical signal is representative of a sensor signal;
generating a second current signal using an amplifier that operates based on the first current signal and a feedback current signal;
digitally sampling the second current signal using an analog to digital converter (ADC) that operates based on the second clock signal to generate a digital signal;
operating a current digital to analog converter (CDAC) that operates based on the second clock signal to generate an updated feedback current signal based on the digital signal, wherein the updated feedback current signal reduces noise sensitivity of the amplifier; and
processing the digital signal to estimate sensor data within the sensor signal.

15. The method of claim 14 further comprising:
operating another CDAC that includes a calibrated static CDAC to generate another feedback current signal based on a static control signal; and
adding the another feedback current signal to the updated feedback current signal to reduce the noise sensitivity of the amplifier.

16. The method of claim 14, wherein the sensor signal is representative of an environmental characteristic that corresponds to:
temperature;
humidity; or barometric pressure.

17. The method of claim 14, wherein the sensor signal is representative of a biomedical characteristic that corresponds to:
- body temperature;
- heart rate;
- respiratory rate; or
- blood pressure.

18. The method of claim 14, wherein the on-chip relaxation oscillator circuit includes an RC oscillator that includes a resistor-capacitor resonant circuit or an LC oscillator that includes an inductor-capacitor resonant circuit.

19. The method of claim 14, wherein the on-chip relaxation oscillator circuit includes a temperature sensor configured to calibrate the first clock signal based on change of environmental temperature.

20. The method of claim 14 further comprising:
- operating a low noise amplifier (LNA) to generate a first differential signal based on the first current signal or a third current signal that is representative of another sensor signal;
- generating a second differential signal using an anti-aliasing filter based on the first differential signal;
- digitally sampling the second differential signal using another ADC that operates based on the second clock signal to generate another digital signal; and
- processing the another digital signal to estimate the sensor data within the sensor signal or to estimate other sensor data within the another sensor signal.

* * * * *